United States Patent [19]

Thomas et al.

[11] Patent Number: 4,565,867

[45] Date of Patent: Jan. 21, 1986

[54] ANHYDROUS HIGH-PRESSURE MELAMINE SYNTHESIS

[75] Inventors: Roger E. Thomas, Baton Rouge; David E. Best, Prairieville, both of La.

[73] Assignee: Melamine Chemicals, Inc., Donaldsonville, La.

[21] Appl. No.: 689,921

[22] Filed: Jan. 9, 1985

Related U.S. Application Data

[63] Continuation of Ser. No. 568,408, Jan. 5, 1984, abandoned.

[51] Int. Cl.$^4$ .......................................... C07D 251/60
[52] U.S. Cl. ................................................... 544/201
[58] Field of Search ....................................... 544/201

[56] References Cited

U.S. PATENT DOCUMENTS

| | | | |
|---|---|---|---|
| 2,549,492 | 4/1951 | Lee | 544/203 |
| 2,566,223 | 8/1951 | Mackay | 544/201 |
| 2,566,224 | 8/1951 | Mackay | 544/203 |
| 2,566,227 | 8/1951 | Paden et al. | 544/203 |
| 2,566,229 | 8/1951 | Mackay | 544/201 |
| 2,575,497 | 11/1951 | Mackay et al. | 544/201 |
| 2,575,498 | 11/1951 | Mackay et al. | 544/201 |
| 2,755,887 | 7/1956 | Boatright | 544/203 |
| 2,760,961 | 8/1956 | Mackay | 544/201 |
| 3,290,308 | 12/1966 | Marten | 544/201 |
| 3,315,442 | 4/1967 | Yuan et al. | 55/70 |
| 3,321,603 | 5/1967 | Hamprecht et al. | 260/555 |
| 3,386,999 | 6/1968 | Manes | 544/203 |
| 3,451,787 | 6/1969 | Marten | 422/235 |
| 3,454,571 | 7/1969 | Kokubo et al. | 260/249.7 |
| 3,470,163 | 9/1969 | Hazelton | 544/201 |
| 3,484,440 | 12/1969 | Kokubo et al. | 544/201 |
| 3,492,302 | 1/1970 | Abe et al. | 544/201 |
| 3,513,167 | 5/1970 | Fromm et al. | 544/203 |
| 3,547,919 | 12/1970 | Hamprecht | 544/203 |
| 3,637,686 | 1/1972 | Kokubo et al. | 544/203 |
| 3,700,672 | 10/1972 | Kokubo et al. | 544/201 |
| 3,723,430 | 3/1973 | Kokubo et al. | 544/201 |
| 4,138,560 | 2/1979 | Hillenbrand et al. | 544/203 |
| 4,348,520 | 9/1982 | Bruls et al | 544/201 |
| 4,408,046 | 10/1983 | Van Hardeveld | 544/201 |

FOREIGN PATENT DOCUMENTS

| | | |
|---|---|---|
| 641643 | 8/1950 | United Kingdom . |
| 1003277 | 9/1965 | United Kingdom . |
| 1032326 | 6/1966 | United Kingdom . |

OTHER PUBLICATIONS

Atsumi Okamoto, "Total Recycle Process Melamine From Urea," *Hydrocarbon Processing,* Nov. 1970, pp. 156-158.

Peter Ellwood, "Process Flowsheet, Lower Investment, Easier Operation to Make Melamine," *Chemical Engineering,* Oct. 19, 1970, pp. 101-103.

*Primary Examiner*—John M. Ford
*Attorney, Agent, or Firm*—A. W. Breiner

[57] ABSTRACT

This high-pressure, high-temperature anhydrous process prepares melamine from urea. It is a primary object of the present invention to provide a highly energy-efficient and improved continuous process for the production of melamine from urea which utilizes a simplified process to produce and recover a high-grade (96 to 99.5% purity) melamine as a dry powder directly from liquid melamine melt. Molten urea is supplied to a reactor maintained at high temperature (700° to 800° F.) and high pressure (1700 to 2200 psig) whereby melamine, $CO_2$, and $NH_3$ are formed. The reactor effluent stream containing liquid melamine, $CO_2$, and $NH_3$ is transferred to a gas separator where $CO_2$ and $NH_3$ containing melamine are separated and cycled to a scrubber unit for scrubbing with molten urea reactant to remove the melamine before transfer of the $CO_2$ and $NH_3$ gases at high pressure to an adjacent urea plant for utilization in producing urea. The melamine liquid product is transferred from the gas separator to a collecting tank maintained at a pressure of less than about 615 psig and from about 120° to 260° F. where the liquid melamine is immediately contacted with, or quenched with a liquid, preferably liquid ammonia. The melamine separates as a dry powder which requires no further processing, having a purity in the range of 96 to 99.5%, useful in applications including fertilizer and resin manufacture. This process is highly cost efficient.

16 Claims, 7 Drawing Figures

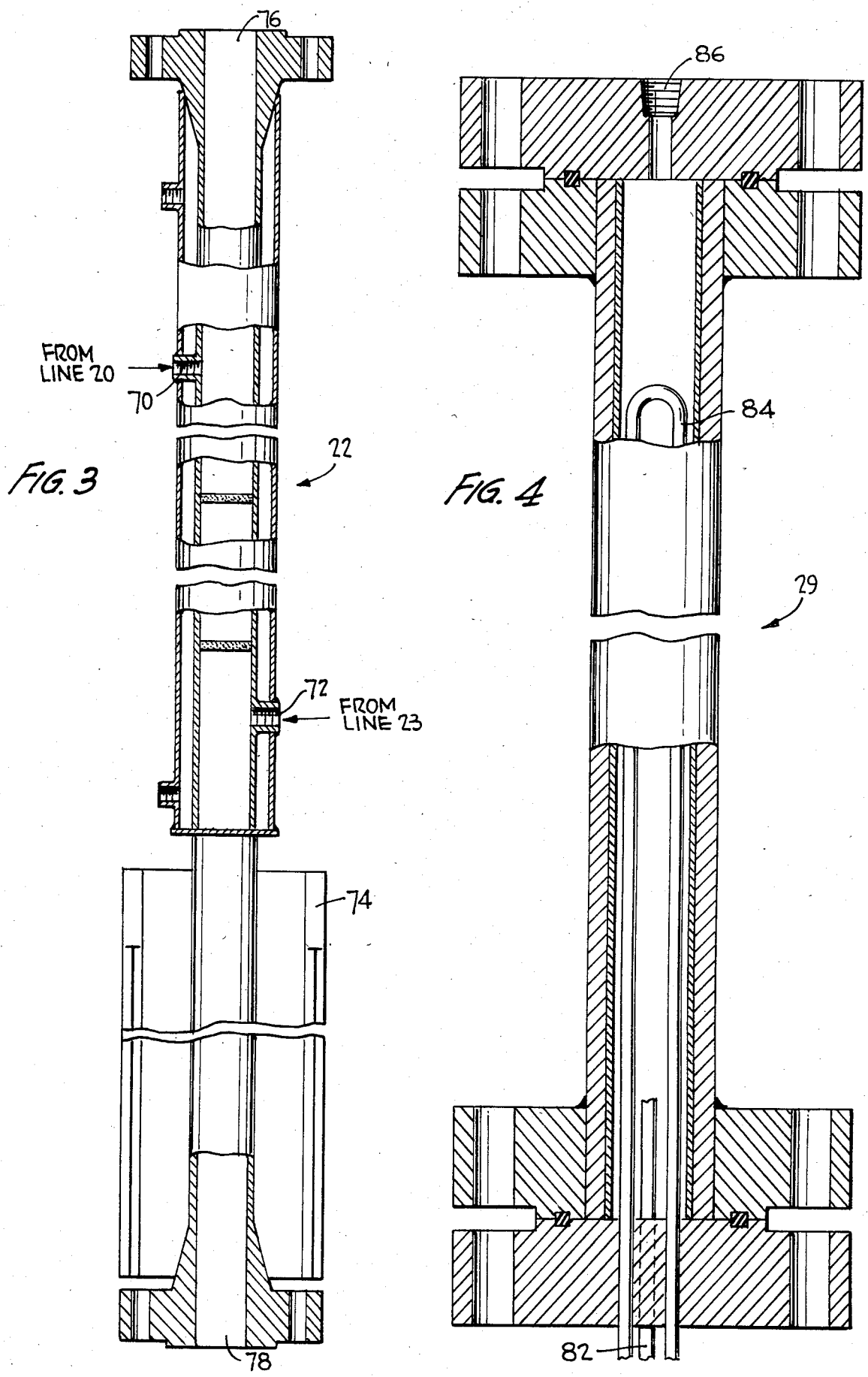

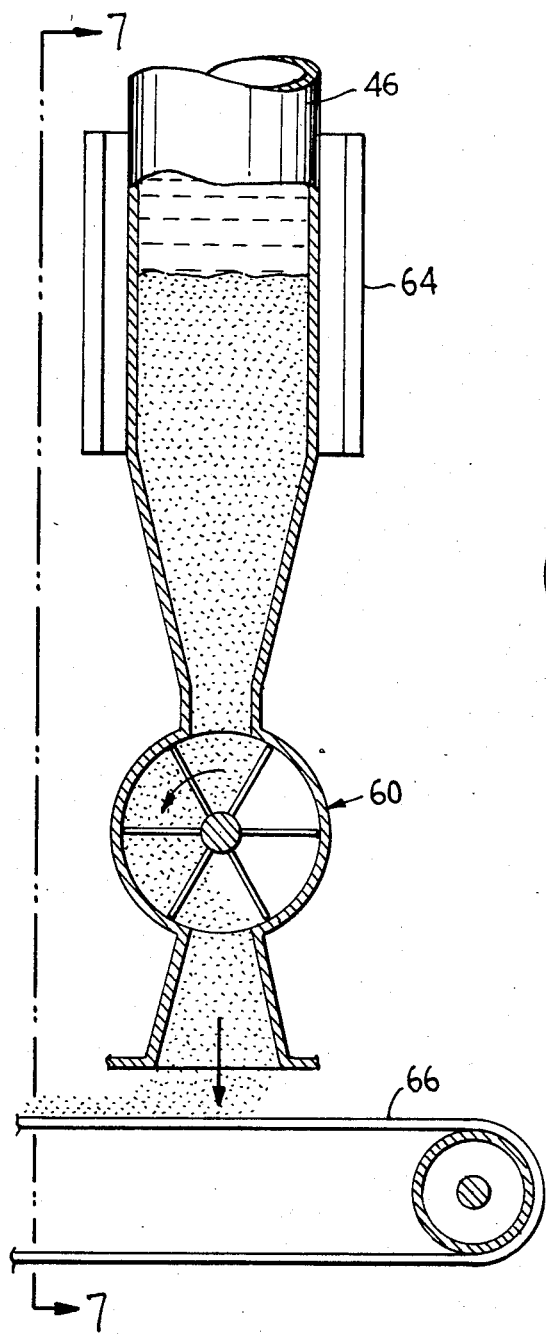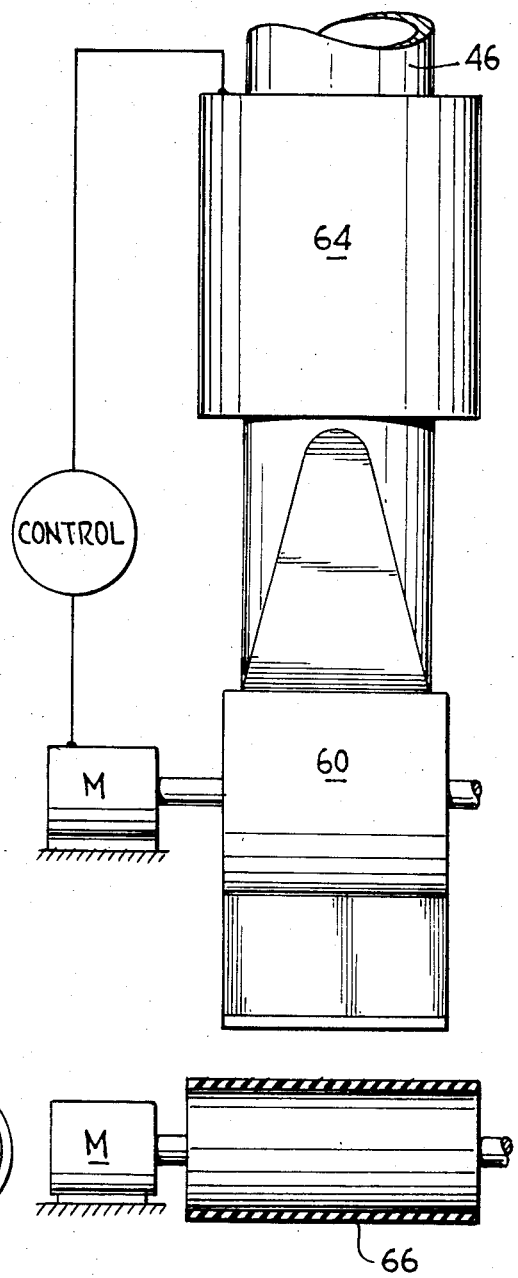

ANHYDROUS HIGH-PRESSURE MELAMINE SYNTHESIS

This is a continuation of application Ser. No. 568,408 filed Jan. 5, 1984, now abandoned.

The present invention is directed to a process for the production of melamine and to the reaction product obtained. More particularly, the invention is directed to a high-pressure, non-catalytic, non-aqueous process of producing melamine from urea wherein the melamine is recovered directly as a dry powder without washing or recrystallization, and to the reaction product obtained.

BACKGROUND OF THE INVENTION AND PRIOR ART

The preferred raw material for production of melamine is urea. Ammonia and carbon dioxide are by-products in the reaction which may be either high pressure and non-catalytic, or low pressure and catalytic using a catalyst such as alumina. The basic reaction is

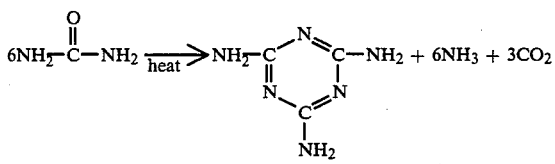

The temperature of the reaction, depending on conditions, will vary but is usually between about 350° and 400° C. (662° to 752° F.). The by-products, ammonia and carbon dioxide, are commonly returned to an adjacent urea plant from which the starting material, a urea melt, is obtained for the melamine reaction. Melamine product is recovered by either a water quench and recrystallization, or by sequential cooling and filtering of the effluent gas from the reaction. The melamine product customarily is at least 99.% pure.

Four commercial processes typify melamine manufacture from urea, i.e., the BASF, Chemie Linz, Nissan, and Stamicarbon procedures. All of the presently practiced commercial processes require substantial energy in the form of steam, electricity, and natural gas. The total energy consumed in these operations varies from 11,000 BTU/lb. melamine product to 23,000 BUT/lb. melamine product. The energy consumed in the reaction of urea to produce melamine is approximately 2200 BTU/lb. The remainder of the energy consumed in the commercial processes is a result of the complexity of the processes and the equipment utilized, and primarily as a result of the separation of the offgas from the product and purification of the product which normally includes a water quench and recrystallization, or a fractional condensation of the melamine and impurities.

In the BASF process melamine is manufactured by heating urea to temperatures of from 350° to 450° C. at atmospheric or low pressures, i.e., up to about 10 atmospheres, in the presence of catalysts and added ammonia. The reactor, built to contain catalyst as well as urea at pressures only slightly above atmospheric, is relatively large. BASF, U.S. Pat. Nos. 4,138,560 and 3,513,167, believed to be directed to the BASF process, describe the melamine as being separated from the reaction gases by fractional condensation, filtration, and cooling the gases to temperatures of from 150° to 250° C. Unreacted urea is removed by further cooling. The by-product ammonia is removed as an offgas from the reactor containing carbon dioxide at slightly above atmospheric pressure. The offgases transferred to the urea synthesis plant at atmospheric pressure is necessarily compressed before use in urea synthesis. It is difficult and costly to bring the offgases to the high reaction pressure required for urea conversion in large-scale production because carbamate can condense if the compression is carried out at relatively low temperature, causing a corrosion problem; and the volume of gases handled can be very large if the compression is carried out at relatively high temperature. The use of alumina catalyst in the BASF process can create problems associated with formation of lumps. Elaborate thermocouple systems in the reactor interior are necessary to forewarn operators of impending hot spots, and the reactors must be shut-down to permit steam feed to remove such lumps. Catalyst escaping from the reactor is removed from the product gases by the use of filters. Heating coils in the reactor are corroded by the severe conditions. The BASF process consumes about 12,000 BTU/lb. melamine formed.

The Chemie Linz process is a two-stage, low-pressure catalytic system. In the first stage urea is decomposed in a fluidized sand bed. Melamine is produced in a second-stage fixed alumina catalyst bed. The melamine product is recovered by quenching the hot reaction gas with cooling aqueous liquor and centrifuging the resulting slurry. Ammonia and carbon dioxide and recovered in two separate streams readily usable for different processes. Ammonia gas is recovered from the offgas at about atmospheric pressure. Carbon dioxide is produced at about 300 psig (20 atms). The Chemie Linz process consumes about 14,500 BUT/lb. melamine product formed.

According to the November 1970 issue of *Hydrocarbon Processing*, the Nissan Chemical process takes place at 100 kg/cm² (94.5 atms) and 400° C. (752° F.) in the absence of a catalyst. Melamine product from the reactor is cooled in a pressure quencher into aqueous ammonia solution. This solution, after separating part of the ammonia at medium pressure, is filtered and reduced to atmospheric pressure in a recrystallizer where the remaining ammonia is separated out and melamine is crystallized out. Melamine crystals separated from the crystallized melamine slurry are centrifuged, dried, and pulverized into the final product. Use of high pressure permits a reduction in the size of the reactor; however, because the mixture is corrosive, the smaller reactors must be made of titanium alloys or other alloys which are non-corrosive. Water is needed to prepare the aqueous ammonia solution used in quenching the reactor product stream, and is needed to wash the melamine crystals in the recrystallization process. According to U.S. Pat. No. 3,454,571, assigned to Nissan Chemical Company, believed to be directed to the Nissan process, an aqueous alkaline solution wash is required to remove impurities adhering to the melamine crystal surface in order to obtain high-grade melamine. The Nissan process consumes about 11,000 BTU/lb. melamine product.

The Stamicarbon melamine process is a low-pressure catalytic system in which melamine is precipitated from the hot reaction gas by quenching rapidly with an aqueous mother liquor. The melamine is purified by dissolving, blending with activated carbon, filtration, and recrystallization. The water is removed by passing the recrystallized product through hydrocyclones, centrifuges, and a pneumatic dryer. After completing these drying steps, the crystalline product is collected. The offgas is produced as a concentrated carbamate solution at 212° F. (100° C.) and 265 psig (18 atms), and returned to the urea synthesis stream. Recycling the carbamate solution to the urea plant introduces additional water to the urea process, reducing conversion to urea. The catalyst in this process must be kept fluidized, and can become agglomerated if cold spots appear causing lumping or condensation of the catalyst. The use of an alumina catalyst requires that makeup catalyst be supplied to the reactor to replace catalyst fines contained in the reaction gas. The Stamicarbon process consumes about 23,000 BTU/lb. melamine product formed.

As is apparent, each of the aforesaid processes suffers disadvantages from a practical standpoint. In the low-pressure system where the melamine goes directly to a vapor without passing through a liquid melamine stage there are few impurities. However, the low-pressure reactor and recovery system are complex, requiring extensive equipment and space, and consume high amounts of energy including as a result of the handling of large volumes of gases. Additionally, since a catalyst is employed, separate problems are presented in the separation or filtration of the product from the catalyst. In the known high-pressure systems where the melamine is first formed as a liquid, substantial amounts of impurities are normally found in the melamine product including significant amounts of melam and melem which are detrimental for the end uses of the melamine product. Accordingly, in the known high-pressure systems it has been necessary to utilize an aqueous quench, recrystallization, and subsequent drying of the melamine product to obtain the necessary degree of purity, requiring complex and space-consuming equipment, as well as high energy consumption.

OBJECTS AND GENERAL DESCRIPTION OF THE INVENTION

It is a primary object of the present invention to provide a highly energy efficient and improved continuous process for the production of melamine from urea which utilizes a surprisingly simplified process to produce and recover a high-grade (96 to 99.5% purity) melamine as a dry powder directly from liquid melamine melt.

The aforesaid and other objects of this invention are accomplished by the presently disclosed continuous, high-pressure, non-catalytic, anhydrous process and plant system for converting urea to liquid melamine and by-product offgas containing carbon dioxide and ammonia wherein the only essential components of the plant system are an offgas scrubber unit, a reactor unit, a separator unit, and a product cooling unit. In carrying out the process, (1) Urea melt is fed into the scrubber at from about 1500 to 2500 psig pressure, preferably from about 1700 to 2200 psig, and at a temperature above the melting point of urea. In the scrubber, the liquid urea contacts reaction offgases principally composed of $CO_2$ and $NH_3$ and containing melamine. The urea, in molten condition, scrubs the melamine from the offgas. In the scrubbing process, the offgases are cooled from about the temperature of the reactor, i.e., from about 670° to 800° F. to from about 350° to 450° F., and the urea is preheated to the 350° to 450° F. temperature range. The temperature and pressure are interrelated. If the pressure is at the low end of the range, i.e., 1500 to 1700 psig, the minimum temperature of the scrubber will vary from about 350° to 360° F.; whereas if the scrubber is at the high end of the pressure range, i.e., 2000 to 2200 psig, the minimum temperature can be increased to about 360° to 380° F. Below the above minimum temperatures ammonia and $CO_2$ condense in the bottom of the scrubber and may form carbamate which can be detrimental. As a rule of thumb, the higher the pressure the higher the required minimum temperature. Above about 500° F. the urea may react to form intermediate products. These intermediate products can be detrimental.

The offgases are removed from the top of the scrubber and preferably recycled to a urea plant for conversion into urea. The preheated urea is taken off the bottom of the scrubber together with the minor amounts of melamine and fed to the reactor at from about 1500 to 2500 psig. The scrubber, in the embodiment shown, is jacketed to provide supplemental cooling in the scrubber for temperature control. It may be desirable to control the temperature of the scrubber by some other heat-transfer means such as coils within the scrubber.

Accordingly, the scrubber performs various functions including driving off of water which may be present in the molten urea feed; preheating of the molten urea with offgas; removing melamine from the offgases to provide melamine-free $CO_2$ and $NH_3$, preferably for recycling to a urea plant at controlled pressure and temperature; and recovering excess heat energy for recycling and subsequent use.

(2) The urea taken from the bottom of the scrubber (scrubber bottoms) is fed to the reactor, preferably with a high-pressure pump. In a preferred embodiment, downstream of the pump, but before entering the reactor, a small quantity of ammonia is injected as a liquid or hot vapor into the line carrying the scrubber bottoms. The ammonia, preferably injected as a hot vapor, acts both as a purge to keep the bottom of the reactor from plugging, and supplies excess ammonia to react with any deammoniation product which may be present. The high-pressure pump can be eliminated, for example, by elevating the scrubber above the reactor.

(3) In the reactor the molten urea is heated to a temperature of 670° to 800° F., preferably at from about 700° to 800° F., at a pressure of from about 1500 to 2500 psig, preferably from about 1700 to 2200 psig, under which conditions the urea reacts to form melamine, ammonia, and carbon dioxide. The reactor can be any of the state of the art high-pressure reactor such as shown in U.S. Pat. No. 3,470,163. The reactor operates full of liquid melamine, with the products from the reactor consisting of liquid melamine, ammonia, and carbon dioxide being continuously fed as a mixed stream to the gas separator.

(4) In the gas separator the liquid melamine is separated from the offgas, and liquid melamine is collected in the bottom of the separator. The separator is held at a temperature above the melting point of melamine, and preferably at the same temperature and pressure as the reactor. The gaseous ammonia and carbon dioxide saturated with melamine vapor are removed overhead and fed into the urea scrubber. The temperature and pressure are controlled in order that the melamine concentration in the scrubber bottoms is not more than about 10% melamine. Normally the lower the operating pressures the greater the amount of melamine removed with the offgases. The liquid melamine is removed from the gas separator on level control and injected into the product cooling unit.

(5) In the product cooling unit the liquid melamine is depressurized and rapidly cooled with a liquid medium. It has been found that impurities, particularly melem and melam, are not formed in the reactor, but are formed primarily in converting the liquid melamine into a usable solid product. Using a liquid medium that is a vapor at the temperature of the product as a quench, dry melamine powder is formed without substantial formation of impurities. The melamine product is removed from the bottom of the cooling unit.

The product cooling unit preferably is maintained at a temperature below the melting point of urea since otherwise if there are urea impurities in the melamine, the urea will go off with the gas formed from gasification of the liquid melamine, i.e., ammonia gas, or could cause stickiness of the separated melamine powder. The minimum temperature is the vapor temperature equilibrium of the liquid quenching agent at the pressure of operation. The liquid quenching agent is a low boiling liquid which gasifies with the gas being readily separated from the melamine product. Suitable quenching agents are ammonia, water, or a low boiling alcohol. However, because of its unique characteristics, including its cooling capacity and favorable vapor pressure, liquid ammonia is a highly preferred quenching medium. The pressure can be atmospheric pressure or a pressure up to about 600 psig. It is preferred to operate at a pressure of about 200 to 400 psig and a temperature of from about 120° to 165° F.

In the presently disclosed process the pressure, as above defined, will be the same in the scrubber, reactor, and gas separator. The temperature of the reactor and the gas separator will also be the same. The offgases removed from the gas separator will be at the same temperature as the reactor and separator until they reach the scrubber where they are cooled in the process of being scrubbed with the molten urea. The liquid melamine transferred from the gas separator enters the product cooling unit at the same temperature as the reactor and gas separator.

In the presently disclosed process it is important that the liquid melamine and offgas from the reactor are transferred from the reactor to the gas separator as a mixed stream, and the offgases and melamine separated in the separator unit. A further important aspect is in the use of a liquid medium to quench the liquid melamine. The quenching with a liquid medium immediately as the liquid melamine enters the product cooling unit eliminates the formation of substantial impurities including melem and melam.

The dry melamine powder recovered directly from the quenching of the liquid melamine in the cooling unit is substantially pure melamine, having a purity of from about 96 to 99.5% melamine or above and, accordingly, can be used directly in most melamine applications without purification. The purity of the recovered melamine, particularly the low levels of melem and melam which comprise no more than about one-half to one and one-half percent melam and melem, is surprising. It was not predicted and is not predictable from the prior art processes that such a high degree of purity would be possible. Moreover, it was determined that the particles of the dry melamine product are in the form of mini-agglomerates. It appears that a number of very small particles, in the form of imperfect crystals, are bonded together to form larger porous particles. Accordingly, the recovered dry melamine product has the high surface area of small particles with the handling characteristics of large particles.

As will be further apparent, the process is surprisingly simple in contrast to the complex, high-energy consuming processes of the heretofore commercial systems. A plant-system constructed in accordance with the present invention designed to produce 200 million pounds of melamine per year can be situated in one-fourth the space of a low-pressure melamine system of the Stamicarbon design where the low-pressure system was designed to have a capacity of only 70 million pounds of melamine per year. Further, the capital cost of a system designed in accordance with the present invention comprises less than about 40% of the capital cost of any of the aforesaid commercial installations. As a result of the simplified process, including the elimination of a need to handle high volumes of gases including high volumes of ammonia, and due to the limited number of pieces of equipment in the plant-system, the process will utilize only approximately 29% of the energy of any of the prior art commercial systems. This is a reduction of over 71% in energy consumption. The economics of the present process from the standpoint of energy consumption relative to the commercial processes noted hereinbefore are shown in Table I as follows:

TABLE I

| | Melamine Process Energy Consumption BTU/lbs. Melamine | | | | |
|---|---|---|---|---|---|
| | BASF | Chemie Linz | Nissan | Stami-carbon | Process of Invention |
| Steam | 1,971 | 6,809 | 2,598 | 7,409 | 94 |
| Electricity | 1,937 | 765 | 1,248 | 671 | 3,180 |
| Natural Gas | 6,000 | 6,300 | 7,100 | 6,800 | — |
| Processing $CO_2 + NH_3$ | 1,935 | 670 | 164 | 8,265 | — |
| TOTAL | 11,843 | 14,544 | 11,110 | 23,145 | 3,274 |

As a result of the economics of the system and primarily the ability to obtain melamine product without the costly steps of washing and recrystallization, new markets are available for the melamine product such as as a high-nitrogen, time-release fertilizer. Heretofore the high cost of melamine precluded it practical application in many fields, including the fertilizer field. Additionally, the melamine product of the present invention has advantageous release characteristics when used as a fertilizer over melamine products formed by a process where the melamine product is washed and recrystallized. It appears that this improved release characteristic is a result of the melamine product forming mini-agglomerates of many small particles formed from crude, imperfect crystals. The mini-agglomerates of imperfect crystals being porous in nature more readily biodegrade and, thus, more readily release the components of the melamine product into the soil.

THE DRAWING AND DETAILED DESCRIPTION OF THE PREFERRED EMBODIMENT

Having described the invention in general terms, a detailed description of a preferred embodiment will be described in relation to the drawing. In the drawing, wherein like numbers represent like elements, FIG. 1 is a flow diagram of a prior art high-pressure system for the production of melamine product from urea;

FIG. 3 is a view partially in section and partially broken away of a scrubber unit suitable for use in accordance with the present invention;

FIG. 4 is a view partially in section and partially broken away of a reactor suitable for use in the present invention;

FIG. 6 is an elevational view partly broken away and partly in section of a collector tank of the product cooling unit; and FIG. 7 is a view of the collector tank of FIG. 6 taken along line 7—7 of FIG. 6.

Figure 1:
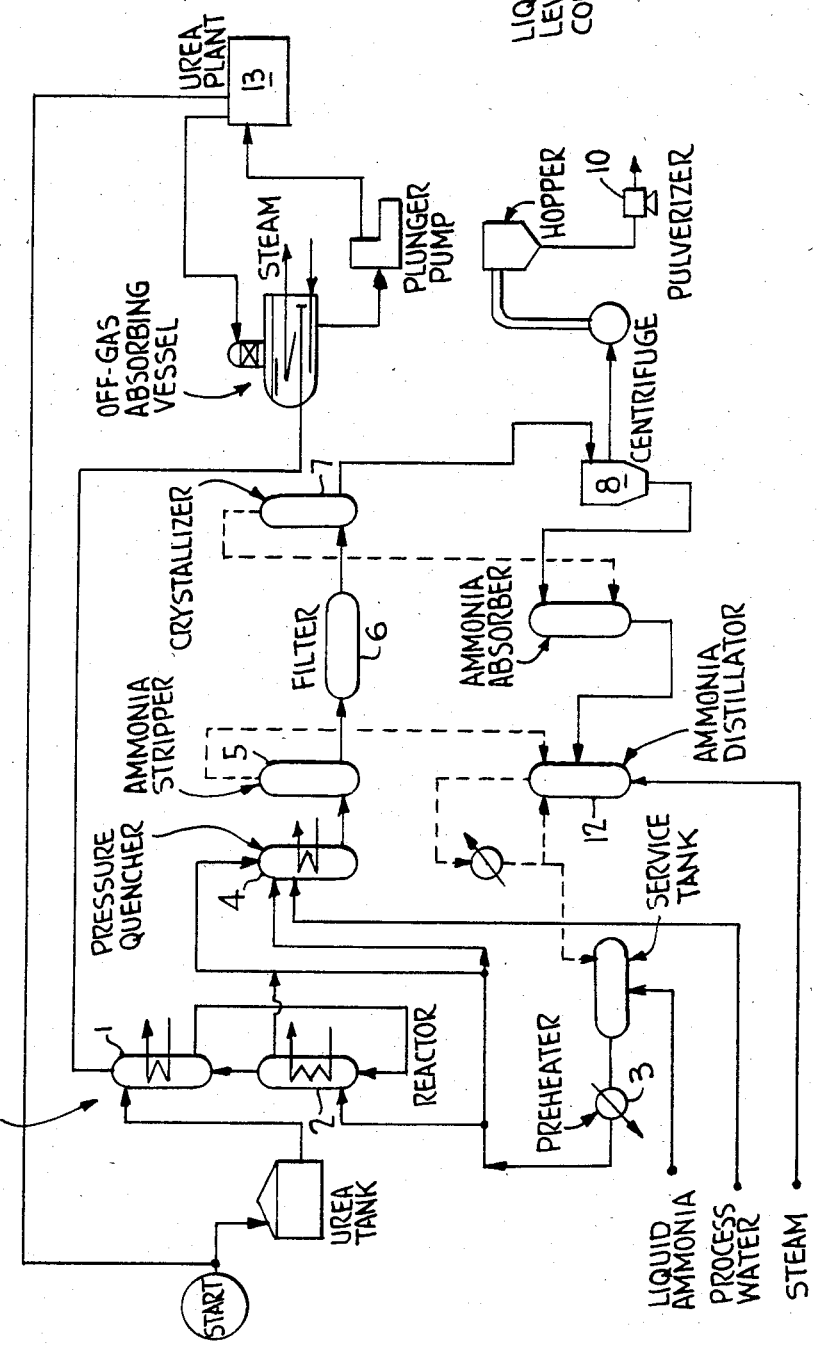

The flow diagram of FIG. 1 is representative of a commercial high-temperaure, high-pressure system for converting urea into melamine product and is taken from an article appearing in *Hydrocarbon Processing*, November 1970, pp. 156–158, entitled "Total Recycle Process Melamine From Urea," authored by Atsumi Okamoto of Nissan Chemical Industries, Inc., Tokyo, Japan. In the process molten urea is compressed to about 100 Kg/cm$^2$ and delivered to the high pressure washing tower (1) and after absorption of melamine vapor contained in the offgas (generated in the synthesis reactor) is fed into the reactor (2). Liquid ammonia is compressed to about 100 Kg/cm$^2$, vaporized to about 400° C. in the preheater (3) and also fed into the reactor (2). Reaction takes place at about 400° C. and 100 Kg/cm$^2$ and the urea is decomposed into an aqueous melamine solution. A molten salt heat-transfer medium is used for the heat supply to the reactor. Melamine offgas from the melamine solution at the upper part of the reactor enters the high-pressure washing tower at reaction pressure, and after being scrubbed with feed urea is returned to the urea plant at about 200° C. and 100 Kg/cm$^2$. Melamine from the reactor (2) is cooled in the pressure quencher (4) into aqueous ammonia solution. This solution, after separating part of the ammonia at medium pressure in the ammonia stripper (5), is filtered at filter unit (6) and reduced to atmospheric pressure in the crystallizer (7), where the remaining ammonia is separated and melamine is crystallized out. Melamine crystals separated from the crystallized melamine slurry in the centrifuge (8) are dried and pulverized (10) into the final product. The ammonia gas separated is recovered in the ammonia absorber (11) and through liquefication after purification by distillation (12), recycled as liquid ammonia. The high-temperature, high pressure and melamine-free offgas can be integrated with a urea plant (13). This high-pressure system is similar to low-pressure systems with respect to the separation and purification of the melamine product taken from the reactor.

Figure 2:
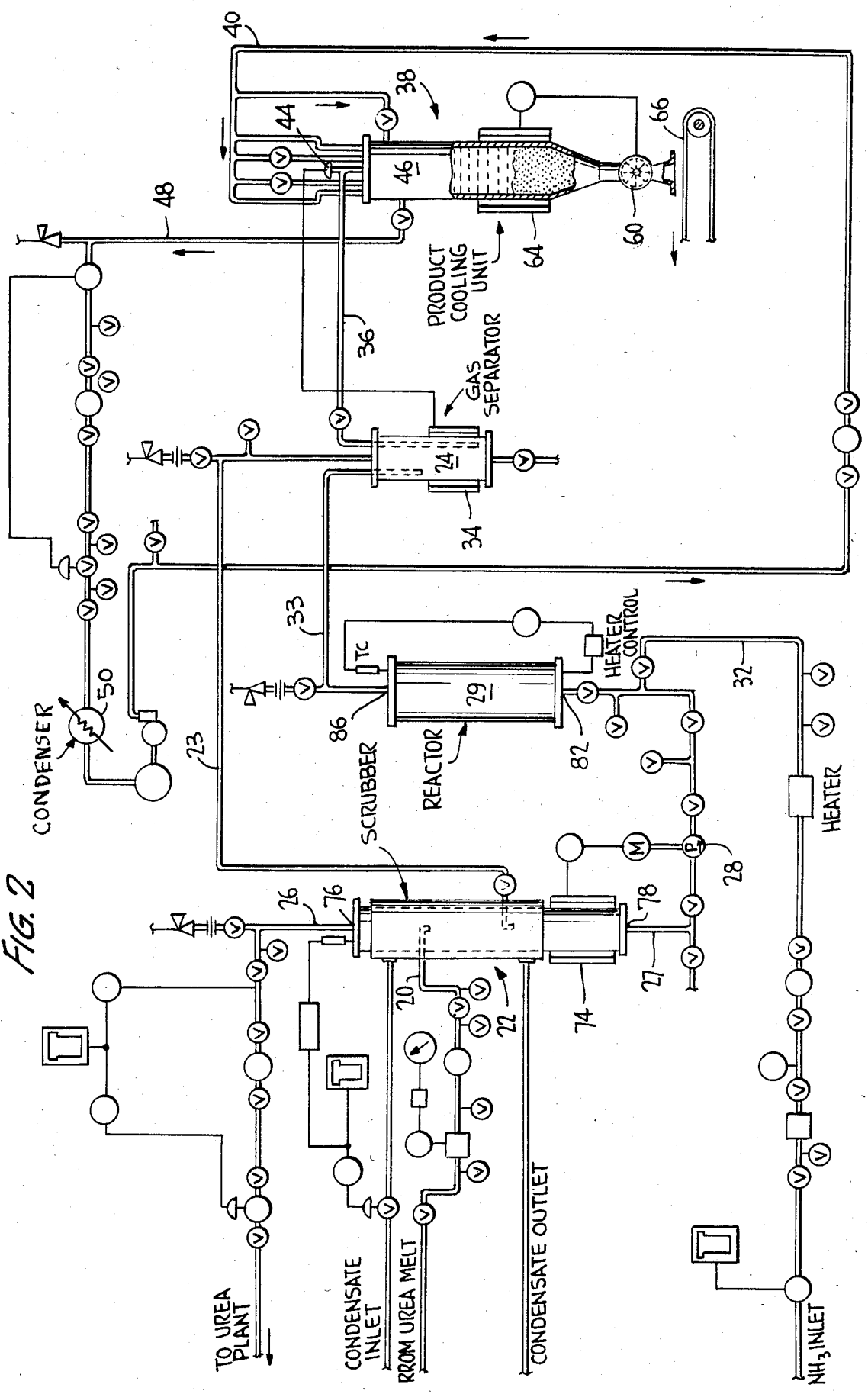
FIG. 2 is a flow diagram of a complete plant-system according to the present invention for the manufacture of melamine product from urea.

The flow diagram of FIG. 2 diagrammatically illustrates the present invention. Urea is fed through line 20 to scrubber unit 22 at a temperature above the melting point of urea, and preferably at about 280° F.; and at a pressure of from about 1700 to 2200 psig. In the continuous process, scrubber unit 22 is also fed through line 23 with offgases from separator 24. The offgases, consisting primarily of ammonia, carbon dioxide, and melamine, will be at a temperature of approximately 700° to 800° F., and at a pressure of from about 1700 to 2200 psig, i.e., the reaction conditions of the reactor and separator unit. The stream composition from the separator to the scrubber unit will be approximately 45 to 65% ammonia, 30 to 50% carbon dioxide, and 3 to 10% melamine. The molten urea will be used to "scrub" the melamine from the offgases, giving off heat energy to preheat the urea and reducing the temperature of the offgases to about 350° to 450° F. The urea containing the melamine will settle at the bottom of the scrubber 22. The purified ammonia and carbon dioxide gases at the reduced temperature is fed through line 26 to a urea plant for utilization in producing urea.

The scrubber bottoms are removed from the bottom of the scrubber and fed through line 27 by means of a pump 28 at a temperature of from about 350° to 450° F., and a pressure of from about 1700 to 2200 psig into reactor 29. Ammonia from a suitable ammonia source is pumped through line 32 into the urea stream from the scrubber. The hot ammonia which is injected into the line carrying the scrubber bottoms acts as a purge to keep the bottom of the reactor from plugging and supplies excess ammonia to react with any deammoniation product which may be present. The reactor will also be maintained at an operating temperature of from about 700° to 800° F., and a pressure of from 1700 to 2200 psig. The reactor, which is resistant to corrosion, i.e., a titanium-clad carbon steel; preferably includes means to circulate the reactant within the reactor. The preferred reactor temperature is about 770° F. and the preferred pressure is 2000 psig. The reactor is temperature controlled using conventional heat control systems including thermocouples.

The product of the reactor, comprised primarily of ammonia, carbon dioxide and melamine, is fed to gas separator 24. The reaction product is released into the separator at a distance approximately one-third from the top of the separator. In the separator the gaseous by-products consisting of ammonia, carbon dioxide and melamine which are fed to the scrubber unit 22 through line 23 are removed from the top of the separator. Liquid melamine is removed from substantially the bottom one-third of the separator controlled by level indicator 34 at a temperature of approximately 700° to 800° F., and a pressure of about 1700 to 2200 psig, and fed through line 36 to the product cooling unit 38. Liquid ammonia is fed through line 40 to cooling unit 38. The liquid melamine is let down through let-down valve 44 into collector tank 46 of cooling unit 38. Immediately upon entering tank 46 which may be at atmospheric or at a higher pressure the melamine contacts liquid ammonia which cools and stabilizes the liquid melamine, transforming the liquid melamine directly into a dry powder. The dry powder is dropped to the bottom of tank 46 while ammonia is released through line 48 and circulated through control valves and a condenser 50 to reliquefy the ammonia, which is then reused as a quenching medium.

In the embodiment shown, the collector tank 46 is maintained under a pressure of about 400 psig and at a temperature of about 150° F. At this pressure and temperature liquid ammonia can be cooled by available cooling water. The solid melamine product is continuously removed from the collector tank through a rotary valve 60 controlled by a level control 64. As a result of maintaining a head of melamine powder above the rotary valve 60 of approximately two to eight feet there is no substantial pressure loss through rotary valve 60. The melamine product is released through rotary valve 60 onto a suitable conveyor 66 for subsequent bagging or the like. The rotary valve is shown in enlarged scale in FIGS. 6 and 7.

The present invention is not directed to specific scrubber units, reactors, or gas separators. Any of the prior art components can be used. However, the scrubber unit can conveniently be a scrubber unit as shown in FIG. 3 wherein the scrubber unit includes a urea inlet 70 into the scrubber 22 leading from urea supply line 20. The molten urea entering inlet 70 will flow downward, and in flowing downward will contact and scrub offgases entering port 72 from line 23 leading from separator unit 24. The level of molten urea containing the melamine product scrubbed from the offgases is controlled in the bottom of the scrubber by level control 74. The offgases are removed through the top of the scrubber through outlet 76 for recycling to a urea plant, and molten urea is removed from the bottom of the scrubber through outlet 78 and fed to the reactor.

A reactor suitable for use in the plant-system of the present invention is illustrated in FIG. 4. The reactor 29 includes an inlet 82 leading from line 32. The reactor is heated by means of a "U" conduit 84 which carries a heat-transfer material, preferably a molten salt, for heating the reactor. A single stream from the reactor which includes the liquid melamine, $CO_2$, and ammonia is removed from the reactor through outlet 86, and flows through line 33 to gas separator 24.

Figure 5:
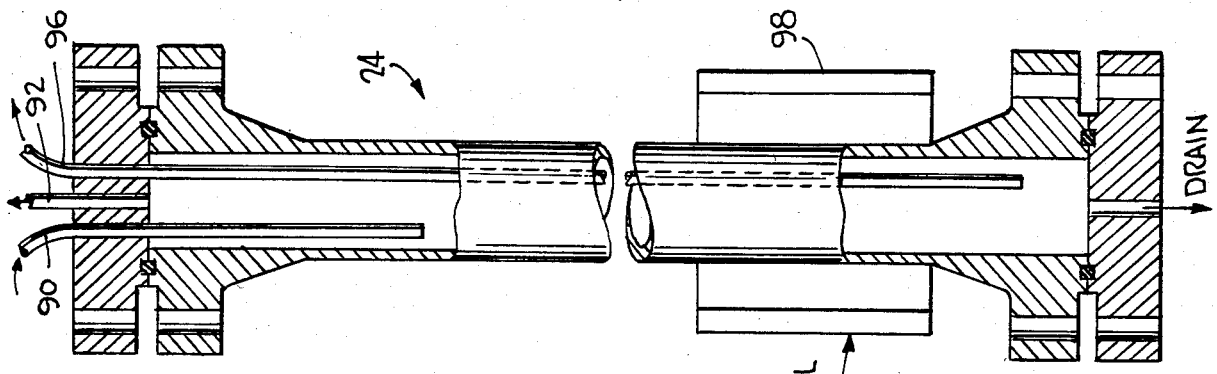
FIG. 5 is a view partially in section and partially broken away of a gas separator suitable for use in accordance with the claimed invention.

The separator unit as illustrated in FIG. 5 comprises an inlet 90 dropping the mixed stream from reactor 29 into the separator. Gaseous components are removed through outlet 92 being fed into line 23 for transfer to scrubber unit 22. The separator unit also includes outlet 96 for removal of melamine for transfer through line 36 to product cooling unit 38. The transfer of liquid melamine to the product cooling unit is controlled by level control means 98.

The invention is further illustrated by the following details of conditions and results of a pilot plant operation which will illustrate the energy efficiency of the process.

Urea is supplied from an adjacent urea plant in line 20 to the scrubber unit 22 at 2000 psig pressure and a temperature of 280° F. After the molten urea is preheated to a temperature of approximately 400° F. with offgases from the separator unit 24, the urea is fed into the bottom of the reactor 29. In the reactor the pressure of 2000 psig is maintained and the urea is heated to a temperature of 770° F. The urea is pyrolyzed into liquid melamine, $CO_2$ and $NH_3$. The reaction products are transferred as a mixed stream to gas separator 24 maintained at 770° F. and 2000 psig. In the separator the reactor product is separated into an offgas stream containing $CO_2$, ammonia, and some melamine which is recycled through line 23 to the scrubber unit 22. The liquid melamine is fed to the product cooling unit 40 at a temperature of 770° F. and 2000 psig pressure, and let down through let-down valve 44 into collector tank 46 which is at a temperature of 169° F. and a pressure of 400 psig. The product is immediately contacted with liquid ammonia through lines 40. The product recovered without washing or recrystallization has a composition as follows:

Melamine: 98.0%
Urea: 0.81%
$NH_3$: —
$CO_2$: 0.03%
Impurities (ammeline-related compounds): 0.05%
Organic Solids (melem and melam, and others): 0.07%

The theoretical conversion based on the urea in the product is 99.19%. The product is recovered from the collector tank as a dry white powder without further washing or recrystallization. The total energy consumed in the product is as set forth in Table I, i.e., 3274 BTU/lb. melamine. The melamine product as a result of the liquid quench has the high surface area of a small particle, but due to the bonding of a number of small particles together has the handling characteristics of a large particle.

As will be apparent to one skilled in the art, various modifications can be made within the scope of the aforesaid description. Such modifications being within the ability of one skilled in the art form a part of the present invention and are embraced by the appended claims.

It is claimed:

1. A continuous process for producing melamine from urea comprising pyrolyzing urea in a reactor at a pressure at from about 1500 to 2500 psig and at a temperature at from about 670° to 800° F. to produce a reaction product containing liquid melamine, $CO_2$ and $NH_3$; transferring, under pressure, said reaction product as a mixed stream to a separator unit; maintaining said separator unit at substantially the same pressure and temperature as said reactor; separating said reaction product in said separator unit into $CO_2$ and $NH_3$ offgases containing melamine vapors and liquid melamine; simultaneously transferring (a) said $CO_2$ and $NH_3$ offgases containing melamine at a temperature and pressure substantially the same as said temperature and pressure of said separator unit to a scrubber unit and scrubbing said off-gases with molten urea to preheat said urea and cool said offgases and remove therefrom said melamine, and thereafter removing $NH_3$ and $CO_2$ gases from said scrubber unit at a temperature of from about 350° to about 450° F. and feeding said preheated molten urea containing said melamine to said reactor, and (b) said liquid melamine to a product cooling unit; and depressurizing and quenching said liquid melamine with a liquid medium which will form a gas at the temperature of said liquid melamine in said product cooling unit to produce a commercially useful solid melamine product, without washing or further purification.

2. The process of claim 1 wherein said melamine product has a purity of from about 96 to 99.5% melamine, and contains not more than about 1.5% melem and melam.

3. The process of claim 1 wherein said reactor is at a pressure of from 1700 to 2200 psig and at a temperature of from 700° to 800° F., said gas separator being maintained at substantially said pressure and temperature of said reactor, and said scrubber being maintained at substantially the same pressure of said reactor.

4. The process of claim 3 wherein said liquid for quenching said liquid melamine is anhydrous liquid ammonia.

5. The process of claim 4 wherein the product cooling unit is maintained at a pressure of from about 200 to 600 psig and at a temperature of from about 120° to 230° F.

6. The process of claim 5 wherein said solid melamine product has a purity of from 97.5 to 99.5% melamine and contains no more than about 0.75% melam and melem.

7. The process of claim 5 wherein said scrubber unit is maintained at a temperature of from about 350° to 380° F.

8. A plant-system for producing melamine from urea comprising as the essential components of said plant-system a reactor unit; a separator unit; a scrubber unit, and a product cooling unit, said reactor unit including: means for heating and maintaining said reactor to a temperature of from about 670° F. to about 800° F.; means for pressurizing said unit to from about 1500 to 2500 psig and pyrolyzing urea to produce liquid melamine, $CO_2$ and $NH_3$, and means for continuously transferring under said temperature and pressure conditions liquid melamine, $CO_2$ and $NH_3$ as a mixed stream to said separator unit;

said separator unit including: means for maintaining said separator at substantially the same temperature and pressure as said reactor; means for receiving and separating under said temperature and pressure conditions said stream of liquid melamine, $NH_3$ and $CO_2$, and means for continuously transferring said $CO_2$ and $NH_3$ offgases containing melamine vapors to said scrubber, and means for continuously transferring said liquid melamine to said product cooling unit;

said scrubber unit including: means for receiving molten urea; means for receiving said offgases containing said melamine from said separator unit at said temperature and pressure conditions of said separator unit; means for contacting said molten urea with said offgases containing melamine to scrub said melamine from said $CO_2$ and $NH_3$ gases and preheating said urea, and means for continuously transferring said molten urea containing said scrubbed melamine to said reactor;

said product cooling unit including: means for receiving said liquid melamine from said separator unit; means for depressurizing and quenching said liquid melamine with a liquid medium which will form a gas at the temperature of said liquid melamine, and collecting said melamine without washing or further purification as a solid at from about 96 to 99.5% melamine.

9. The plant-system of claim 8 wherein said liquid medium for quenching said liquid melamine is liquid ammonia.

10. The plant-system of claim 9 wherein said product cooling unit includes a pressurized product collector tank including valve means at one end and said liquid melamine is received through said valve means by said tank.

11. The plant-system of claim 10 wherein said collector tank further includes a discharge end, said discharge end including valve means and a product level indicator constructed and arranged with said valve means; said tank containing a head of at least about 2 to 8 feet of solid melamine product, and means for automatically controlling the valve means in conjunction with said level indicator to continuously remove powdered melamine from the collector tank in response to said level indicator.

12. In a continuous high-pressure, non-catalytic process for producing melamine product by pyrolyzing urea to produce $NH_3$, $CO_2$ and melamine, the improvement wherein the melamine is in the liquid phase and is quenched by contacting the melamine with liquid ammonia which at the temperature of said melamine will form a gas to provide a solid melamine product, and recovering said melamine product without further washing or purification as a solid containing from about 96 to 99.5% melamine and not more than about 1.5% melem and melam.

13. In the process of claim 12 the further improvement wherein said melamine is liquid.

14. The process of claim 13 wherein said urea is pyrolyzed in a reactor maintained at a temperature of from about 700° to 800° F. and a pressure of from about 1700 to 2200 psig.

15. The process of claim 14 wherein said quenching of liquid melamine with liquid ammonia is carried out at a pressure of from about 200 to 600 psig and a temperature of from about 120° to 230° F.

16. The process of claim 15 wherein said solid melamine product has a purity of from 97.5 to 99% melamine and contains no more than about 0.75% melam or melem.

* * * * *